– 
United States Patent [19]

Axen

[11] 4,246,197

[45] Jan. 20, 1981

[54] 6-KETO-PGE$_1$ AMIDES

[75] Inventor: Udo F. Axen, Plainwell, Mich.

[73] Assignee: The Upjohn Company, Kalamazoo, Mich.

[21] Appl. No.: 70,225

[22] Filed: Aug. 27, 1979

Related U.S. Application Data

[60] Division of Ser. No. 829,679, Sep. 2, 1977, Pat. No. 4,205,178, and a continuation-in-part of Ser. No. 755,675, Dec. 30, 1976, abandoned.

[51] Int. Cl.$^3$ .......................................... C07C 103/19
[52] U.S. Cl. .................................. 564/169; 564/189
[58] Field of Search .......... 260/557 R, 558 R, 559 R

[56] References Cited

U.S. PATENT DOCUMENTS 4,187,224   2/1980   Axen .................................. 542/426

OTHER PUBLICATIONS

Corey et al., J. Am. C. Soc., 92, (1970), pp. 397–398.

Primary Examiner—Arthur P. Demers
Attorney, Agent, or Firm—Robert A. Armitage

[57] ABSTRACT

Prostaglandin E (PGE)-type derivatives and analogs having a 6-keto feature are disclosed, including processes for preparing them and the appropriate intermediates, said derivatives having pharmacological activity.

37 Claims, No Drawings

6-KETO-PGE₁ AMIDES

CROSS REFERENCE TO RELATED APPLICATIONS

This application is a divisional application of co-pending application Ser. No. 829,679 filed Sept. 2, 1977, now U.S. Pat. No. 4,205,178; which is a continuation-in-part of Ser. No. 755,675, filed Dec. 30, 1976, now abandoned.

BACKGROUND OF THE INVENTION

The present invention relates to novel 6-Keto-PGE₁ amides which are useful agents for the induction of prostacyclin-like pharmacological effects. Accordingly, these compounds are useful for pharmacological purposes for which prostacyclin and related substances are employed. The essential material constituting disclosure of the preparation and use of these novel compounds is incorporated here by reference from Ser. No. 829,679, filed Sept. 2, 1977.

SUMMARY OF THE INVENTION

The present invention particularly provides a compound of the formula

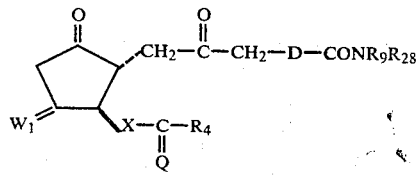

wherein $W_1$ is $\alpha$-OH:$\beta$-H, $\alpha$-H:$\beta$-OH, $\alpha$-H:$\beta$-H, methylene, or $\alpha$-CH₂OH:$\beta$-H;

wherein Q is oxo, $\alpha$-H:$\beta$-H, $\alpha$-R₈:$\beta$-OH, or $\alpha$-OH:$\beta$-R₈ wherein R₈ is hydrogen or alkyl of one to 4 carbon atoms, inclusive;

wherein R₄ is
(1) —C(R₅) (R₆)—C$_g$H$_{2g}$—CH₃
(2) —C(R₅) (R₆)—Z—(Ph) or
(3) cis—CH₂—CH=CH—CH₂CH₃, wherein C$_g$H$_{2g}$ is alkylene of one to 9 carbon atoms, inclusive, with one to 5 carbon atoms, inclusive, in the chain between —CR₅R₆— and terminal methyl, wherein R₅ and R₆ are hydrogen, alkyl of one to 4 carbon atoms, inclusive, or fluoro, being the same or different, with the proviso that one of R₅ and R₆ is fluoro only when the other is hydrogen or fluoro and the further proviso that neither R₅ nor R₆ is fluoro Z is oxa (—O—); wherein Z represents an oxa atom (—O—) or C$_j$H$_{2j}$, wherein C$_j$H$_{2j}$ is a valence bond or alkylene of one to 9 carbon atoms, inclusive, with one to 6 carbon atoms, inclusive between CR₅R₆— and the (Ph); wherein (Ph) is phenyl or phenyl substituted by (T)s, wherein T is alkyl of one to 4 carbon atoms, inclusive, fluoro, chloro, trifluoromethyl, or —OR₇— wherein R₇ is alkyl of one to 4 carbon atoms, inclusive; and wherein s is zero, one, 2 or 3, with the proviso that not more than two T's are other than alkyl and when s is 2 or 3 the T's are either the same or different;

wherein R$_g$ is hydrogen, methyl, or ethyl; and wherein R₂₈ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein D is
(1) —(CH₂)$_d$—C(R₂)₂—
(2) —CH₂—O—CH₂—Y— or
(3) —CH₂—CH=CH—
wherein d is zero to 5, R₂ is hydrogen, methyl, or fluoro, being the same or different with the proviso that one R₂ is not methyl when the other is fluoro, and Y is a valence bond, —CH₂— or —(CH₂)₂—, wherein R₉ is hydrogen, methyl or ethyl and R₂₈ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and wherein X is
(1) trans—CH=CH—
(2) cis—CH=CH—
(3) —C≡C—
(4) —CH₂CH₂—.

With regard to the divalent substituents described above, e.g., Q and W₁, these divalent radicals are defined as $\alpha$-R$_i$:$\beta$-R$_j$, where R$_i$ represents a substituent of the divalent moiety of the alpha configuration with respect to the cyclopentane rings and R$_j$ represents a substituent of the divalent moiety of the beta configuration with respect to the cyclopentane ring. Accordingly, when Q is defined as $\alpha$-OH:$\beta$-R₈, the hydroxy of the Q moiety is in the alpha configuration, i.e. as in prostacyclin, and the R₈ substitutent is in the beta configuration. Not all carbon atoms to which such divalent moieties are attached represent asymmetric centers. For example, when both valence bonds are to hydrogen (e.g., W₁ or Q is $\alpha$-H:$\beta$-H), then no asymmetric center is present.

DESCRIPTION OF THE PREFERRED EMBODIMENTS

The present invention particularly relates to the following chemical compounds:
6,15-diketo-PGE₁ amide;
6-keto-PGE₁ amide;
16,16-dimethyl-6-keto-PGE₁ amide;
16-phenoxy-17,18,19,20-tetranor-6-keto-PGE₁ amide;
16-phenyl-17,18,19,20-tetranor-6-keto-PGE₁ amide;
17-phenyl-18,19,20-trinor-6-keto-PGE₁ amide;
15(S)-15-methyl-6-keto-PGE₁ amide;
15(R)-15-methyl-6-keto-PGE₁ amide;
6-keto-13,14-didehydro-PGE₁ amide;
6-keto-13,14-didehydro-(15R)-PGE₁ amide;
6-keto-13,14-dihydro-PGE₁ amide;
2,2-difluoro-6-keto-PGE₁ amide;
2,2-difluoro-16,16-dimethyl-6-keto-PGE₁ amide;
2,2-difluoro-16-phenoxy-17,18,19,20-tetranor-6-keto-PGE₁ amide;
2,2-difluoro-(15S)-15-methyl-6-keto-PGE₁ amide;
2,2-difluoro-13,14-didehydro-6-keto-PGE₁ amide; and
2,2-difluoro-13,14-dihydro-6-keto-PGE₁ amide.

I claim:
1. A compound of the formula

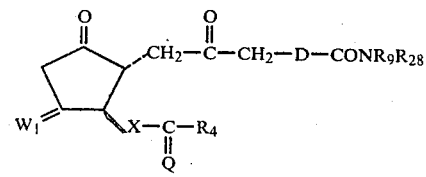

wherein $W_1$ is $\alpha$-OH:$\beta$-H, $\alpha$-H:$\beta$-OH, $\alpha$-H:$\beta$-H, methylene, or $\alpha$-CH$_2$OH: $\beta$-H;

wherein Q is oxo, $\alpha$-H:$\beta$-H, $\alpha$-R$_8$:$\beta$, -OH, or $\alpha$-OH:$\beta$-R$_8$ wherein R$_8$ is hydrogen or alkyl of one to 4 carbon atoms, inclusive;

wherein R$_4$ is
- (1) —C(R$_5$) (R$_6$)—C$_g$H$_{2g}$—CH$_3$
- (2) —C(R$_5$) (R$_6$)—Z—(Ph) or
- (3) cis—CH$_2$—CH=CH—CH$_2$CH$_3$, wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$, wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by (T)s, wherein T is alkyl of one to 4 carbon atoms, inclusive, fluoro, chloro, trifluoromethyl, or —OR$_7$— wherein R$_7$ is alkyl of one to 4 carbon atoms, inclusive; and wherein s is zero, one, 2 or 3, with the proviso that not more than two T's are other than alkyl and when s is 2 or 3 the T's are either the same or different.

wherein D is
- (1) —(CH$_2$)$_d$—C(R$_2$)$_2$—
- (2) —(CH$_2$—O—CH$_2$—Y— or
- (3) —CH$_2$—CH=CH— wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—, wherein R$_9$ is hydrogen, methyl or ethyl and R$_{28}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive; and and wherein X is
- (1) trans—CH=CH—
- (2) cis—CH=CH—
- (3) —C≡C—
- (4) —CH$_2$CH$_2$—

2. A compound according to claim 1 wherein $W_1$ is $\alpha$-OH:$\beta$-H.

3. A compound according to claim 2 wherein D is —(CH$_2$)d—C(R$_2$)$_2$— wherein d and R$_2$ are as defined in claim 1.

4. A compound according to claim 3 wherein D is —(CH$_2$)$_3$—.

5. A compound according to claim 4 wherein X is trans—CH=CH—.

6. A compound according to claim 5 wherein Q is oxo.

7. 6,15-Diketo-PGE$_1$ amide, a compound according to claim 6.

8. A compound according to claim 5 wherein Q is $\alpha$-OH:$\beta$-R$_8$, wherein R$_8$ is hydrogen, methyl or ethyl.

9. A compound according to claim 8 wherein R$_8$ is hydrogen.

10. 6-Keto-PGE$_1$ amide, a compound according to claim 9.

11. 16,16-Dimethyl-6-keto-PGE$_1$ amide, a compound according to claim 9.

12. 16-Phenoxy-17,18,19,20-tetranor-6-keto-PGE$_1$ amide, a compound according to claim 10.

13. 16-Phenyl-17,18,19,20-tetranor-6-keto-PGE$_1$ amide, a compound according to claim 11.

14. 17-Phenyl-18,19,20-trinor-6-keto-PGE$_1$ amide, a compound according to claim 11.

15. A compound according to claim 9 wherein R$_8$ is methyl.

16. 15(S)-15-Methyl-6-keto-PGE$_1$ amide, a compound according to claim 15.

17. A compound according to claim 5 wherein Q is $\alpha$-R$_8$:$\beta$-OH, wherein R$_8$ is hydrogen, methyl or ethyl.

18. (15R)-15-Methyl-6-keto-PGE$_1$ amide, a compound according to claim 17.

19. A compound according to claim 4 wherein X is —C≡C—.

20. A compound according to claim 19 wherein Q is $\alpha$-OH:$\beta$-R$_8$, wherein R$_8$ is hydrogen, methyl or ethyl.

21. 6-Keto-13,14-didehydro-PGE$_1$ amide, a compound according to claim 20.

22. A compound according to claim 19 wherein Q is $\alpha$-R$_8$:$\beta$-OH wherein R$_8$ is hydrogen, methyl or ethyl.

23. 6-Keto-13,14-didehydro-(15R)-PGE$_1$ amide, a compound according to claim 22.

24. A compound according to claim 4 wherein X is —CH$_2$CH$_2$—.

25. 6-Keto-13,14-dihydro-PGE$_1$ amide, a compound according to claim 24.

26. A compound according to claim 3 wherein D is —(CH$_2$)$_2$—CF$_2$—.

27. A compound according to claim 26 wherein X is trans—CH=CH—.

28. A compound according to claim 27 wherein Q is $\alpha$-OH:$\beta$-H.

29. 2,2-Difluoro-6-keto-PGE$_1$ amide, a compound according to claim 28.

30. 2,2-Difluoro-16,16-dimethyl-6-keto-PGE$_1$ amide, a compound according to claim 28.

31. 2,2-Difluoro-16-phenoxy-17,18,19,20-tetranor-6-keto-PGE$_1$ amide, a compound according to claim 28.

32. A compound according to claim 27 wherein Q is $\alpha$-OH:$\beta$-CH$_3$.

33. 2,2-Difluoro-(15S)-15-methyl-6-keto-PGE$_1$ amide, a compound according to claim 32.

34. A compound according to claim 26 wherein X is —C≡C—.

35. 2,2-Difluoro-13,14-didehydro-6-keto-PGE$_1$ amide, a compound according to claim 34.

36. A compound according to claim 26 wherein X is —CH$_2$CH$_2$—.

37. 2,2-Difluoro-13,14-dihydro-6-keto-PGE$_1$ amide, a compound according to claim 36.

* * * * *

UNITED STATES PATENT OFFICE
CERTIFICATE OF CORRECTION

Patent No. 4,246,197      Dated 20 January 1981

Inventor(s) Udo F. Axen

It is certified that error appears in the above-identified patent and that said Letters Patent are hereby corrected as shown below:

Column 1, lines 20-21, "Ser. No. 829,679, filed September 2, 1977" should read -- U.S. Patent 4,205,178 --.

Column 1, line 51, "$R_5$ nor $R_6$ is fluoro Z" should read -- $R_5$ nor $R_6$ is fluoro when Z --; line 64, "Rg is hydrogen," should read -- $R_9$ is hydrogen, --;

Column 3, line 3, "$\alpha$-$R_8$:$\beta$, -OH," should read -- $\alpha$-$R_8$:$\beta$-OH, --; line 36, "-($CH_2$-O-$CH_2$-Y-" should read -- -$CH_2$-O-$CH_2$-Y- --; line 50, "-C=C-" should read -- -C≡C- --.

Signed and Sealed this

Twenty-sixth Day of May 1981

[SEAL]

*Attest:*

RENE D. TEGTMEYER

*Attesting Officer*     *Acting Commissioner of Patents and Trademarks*